US008077963B2

(12) United States Patent
Wang et al.

(10) Patent No.: US 8,077,963 B2
(45) Date of Patent: *Dec. 13, 2011

(54) MOBILE ROBOT WITH A HEAD-BASED MOVEMENT MAPPING SCHEME

(76) Inventors: Yulun Wang, Goleta, CA (US); Charles S. Jordan, Santa Barbara, CA (US); Keith P. Laby, Santa Barbara, CA (US); Jonathan Southard, Santa Barbara, CA (US); Marco Pinter, Santa Barbara, CA (US); Brian Miller, Santa Barbara, CA (US)

( * ) Notice: Subject to any disclaimer, the term of this patent is extended or adjusted under 35 U.S.C. 154(b) by 1114 days.

This patent is subject to a terminal disclaimer.

(21) Appl. No.: 10/890,891

(22) Filed: Jul. 13, 2004

(65) Prior Publication Data

US 2006/0013469 A1    Jan. 19, 2006

(51) Int. Cl.
*G06K 9/00* (2006.01)
(52) U.S. Cl. .............. 382/153; 901/8; 901/16; 700/245; 318/568.12
(58) Field of Classification Search .................... 382/153
See application file for complete search history.

(56) References Cited

U.S. PATENT DOCUMENTS

| | | | |
|---|---|---|---|
| 3,821,995 A | 7/1974 | Aghnides |
| 4,413,693 A | 11/1983 | Derby |
| 4,471,354 A | 9/1984 | Smith |
| 4,519,466 A | 5/1985 | Shiraishi |
| 4,638,445 A | 1/1987 | Mattaboni |
| 4,697,472 A | 10/1987 | Hiyane |
| 4,709,265 A | 11/1987 | Silverman et al. |
| 4,733,737 A | 3/1988 | Falamak |
| 4,751,658 A | 6/1988 | Kadonoff et al. |
| 4,777,416 A | 10/1988 | George, II et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,974,607 A | 12/1990 | Miwa |
| 4,977,971 A | 12/1990 | Crane, III et al. |

(Continued)

FOREIGN PATENT DOCUMENTS

CA    2289697 A1    11/1998

(Continued)

OTHER PUBLICATIONS

Han et al., "Construction of an Omnidirectional Mobile Robot Platform Based on Active Dual-Wheel Caster Mechnisms and Development of a Control Simulator," 2000, Kluwer Academic Publishers, vol. 29, pp. 257-275.*

(Continued)

*Primary Examiner* — John Lee
(74) *Attorney, Agent, or Firm* — InTouch Technologies, Inc.; Paul Evans

(57) ABSTRACT

A robotic system that includes a mobile robot and a remote input device. The input device may be a joystick that is used to move a camera and a mobile platform of the robot. The system may operate in a mode where the mobile platform moves in a camera reference coordinate system. The camera reference coordinate system is fixed to a viewing image provided by the camera so that movement of the robot corresponds to a direction viewed on a screen. This prevents disorientation during movement of the robot if the camera is panned across a viewing area.

5 Claims, 8 Drawing Sheets

U.S. PATENT DOCUMENTS

| | | |
|---|---|---|
| 5,006,988 A | 4/1991 | Borenstein et al. |
| 5,040,116 A | 8/1991 | Evans et al. |
| 5,073,749 A | 12/1991 | Kanayama |
| 5,084,828 A | 1/1992 | Kaufman et al. |
| 5,130,794 A | 7/1992 | Ritchey |
| 5,155,684 A * | 10/1992 | Burke et al. .................. 701/25 |
| 5,157,491 A | 10/1992 | Kassatly |
| 5,186,270 A | 2/1993 | West |
| 5,217,453 A | 6/1993 | Wilk |
| 5,236,432 A | 8/1993 | Matsen, II et al. |
| 5,319,611 A | 6/1994 | Korba |
| 5,341,242 A | 8/1994 | Gilboa et al. |
| 5,341,854 A | 8/1994 | Zezulka et al. |
| 5,366,896 A | 11/1994 | Margrey et al. |
| 5,374,879 A | 12/1994 | Pin et al. |
| 5,419,008 A | 5/1995 | West |
| 5,441,047 A | 8/1995 | David et al. |
| 5,442,728 A | 8/1995 | Kaufman et al. |
| 5,462,051 A | 10/1995 | Oka et al. |
| 5,539,741 A | 7/1996 | Barraclough et al. |
| 5,544,649 A | 8/1996 | David et al. |
| 5,553,609 A | 9/1996 | Chen et al. |
| 5,572,229 A | 11/1996 | Fisher |
| 5,630,566 A | 5/1997 | Case |
| 5,636,218 A | 6/1997 | Ishikawa et al. |
| 5,684,695 A | 11/1997 | Bauer |
| 5,701,904 A | 12/1997 | Simmons et al. |
| 5,739,657 A * | 4/1998 | Takayama et al. ............ 318/587 |
| 5,762,458 A | 6/1998 | Wang et al. |
| 5,786,846 A | 7/1998 | Hiroaki |
| 5,802,494 A | 9/1998 | Kuno |
| 5,836,872 A | 11/1998 | Kenet et al. |
| 5,838,575 A | 11/1998 | Lion |
| 5,857,534 A | 1/1999 | DeVault et al. |
| 5,867,653 A | 2/1999 | Aras et al. |
| 5,917,958 A | 6/1999 | Nunally et al. |
| 5,927,423 A | 7/1999 | Wada et al. |
| 5,959,423 A | 9/1999 | Nakanishi et al. |
| 5,966,130 A | 10/1999 | Benman, Jr. |
| 5,974,446 A | 10/1999 | Sonnenreich et al. |
| 6,006,946 A | 12/1999 | Williams et al. |
| 6,036,812 A | 3/2000 | Williams et al. |
| 6,133,944 A | 10/2000 | Braun et al. |
| 6,135,228 A | 10/2000 | Asada et al. |
| 6,170,929 B1 | 1/2001 | Wilson et al. |
| 6,175,779 B1 | 1/2001 | Barrett |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,256,556 B1 | 7/2001 | Zenke |
| 6,259,806 B1 | 7/2001 | Green |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,321,137 B1 | 11/2001 | De Smet |
| 6,325,756 B1 | 12/2001 | Webb et al. |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,408,230 B2 | 6/2002 | Wada |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,452,915 B1 | 9/2002 | Jorgensen |
| 6,463,361 B1 | 10/2002 | Wang et al. |
| 6,466,844 B1 | 10/2002 | Ikeda et al. |
| 6,468,265 B1 | 10/2002 | Evans et al. |
| 6,474,434 B1 | 11/2002 | Bech |
| 6,491,701 B2 | 12/2002 | Tierney et al. |
| 6,496,099 B2 | 12/2002 | Wang et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 * | 3/2003 | Allard ........................... 700/259 |
| 6,540,039 B1 | 4/2003 | Yu et al. |
| 6,543,899 B2 | 4/2003 | Covannon et al. |
| 6,549,215 B2 | 4/2003 | Jouppi |
| 6,587,750 B2 | 7/2003 | Gerbi et al. |
| 6,594,552 B1 | 7/2003 | Nowlin et al. |
| 6,604,019 B2 | 8/2003 | Ahlin et al. |
| 6,604,021 B2 | 8/2003 | Imai et al. |
| 6,646,677 B2 | 11/2003 | Noro et al. |
| 6,684,129 B2 | 1/2004 | Salisbury et al. |
| 6,691,000 B2 | 2/2004 | Nagai et al. |
| 6,710,797 B1 | 3/2004 | McNelley et al. |
| 6,728,599 B2 | 4/2004 | Wang et al. |
| 6,764,373 B1 | 7/2004 | Osawa et al. |
| 6,781,606 B2 | 8/2004 | Jouppi |
| 6,784,916 B2 | 8/2004 | Smith |
| 6,785,589 B2 | 8/2004 | Eggenberger et al. |
| 6,799,065 B1 | 9/2004 | Niemeyer |
| 6,799,088 B2 | 9/2004 | Wang et al. |
| 6,804,656 B1 | 10/2004 | Rosenfeld et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 * | 1/2005 | Allard ........................... 700/259 |
| 6,852,107 B2 | 2/2005 | Wang et al. |
| 6,871,117 B2 | 3/2005 | Wang et al. |
| 6,879,879 B2 | 4/2005 | Jouppi et al. |
| 6,892,112 B2 | 5/2005 | Wang et al. |
| 6,895,305 B2 | 5/2005 | Lathan et al. |
| 6,914,622 B1 | 7/2005 | Smith et al. |
| 6,925,357 B2 | 8/2005 | Wang et al. |
| 6,995,664 B1 | 2/2006 | Darling |
| 7,092,001 B2 | 8/2006 | Schulz |
| 7,115,102 B2 | 10/2006 | Abbruscato |
| 7,129,970 B2 | 10/2006 | James et al. |
| 7,154,526 B2 | 12/2006 | Foote et al. |
| 7,155,306 B2 | 12/2006 | Haitin et al. |
| 7,158,859 B2 | 1/2007 | Wang et al. |
| 7,158,860 B2 | 1/2007 | Wang et al. |
| 7,161,322 B2 | 1/2007 | Wang et al. |
| 7,164,969 B2 | 1/2007 | Wang et al. |
| 7,171,286 B2 | 1/2007 | Wang et al. |
| 7,174,238 B1 | 2/2007 | Zweig |
| 7,184,559 B2 | 2/2007 | Jouppi |
| 7,215,786 B2 | 5/2007 | Nakadai |
| 7,256,708 B2 | 8/2007 | Rosenfeld |
| 7,262,573 B2 | 8/2007 | Wang et al. |
| 7,346,429 B2 | 3/2008 | Goldenberg et al. |
| 2001/0002448 A1 | 5/2001 | Wilson et al. |
| 2001/0010053 A1 | 7/2001 | Ben-Shachar et al. |
| 2001/0037163 A1 | 11/2001 | Allard |
| 2001/0054071 A1 | 12/2001 | Loeb |
| 2002/0015296 A1 | 2/2002 | Howell |
| 2002/0027597 A1 | 3/2002 | Sachau |
| 2002/0049517 A1 | 4/2002 | Ruffner |
| 2002/0057279 A1 * | 5/2002 | Jouppi ........................... 345/619 |
| 2002/0058929 A1 | 5/2002 | Green |
| 2002/0063726 A1 | 5/2002 | Jouppi |
| 2002/0095238 A1 | 7/2002 | Ahlin et al. |
| 2002/0104094 A1 | 8/2002 | Alexander et al. |
| 2002/0120362 A1 | 8/2002 | Lathan et al. |
| 2002/0130950 A1 | 9/2002 | James et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang et al. |
| 2002/0184674 A1 | 12/2002 | Xi et al. |
| 2003/0030397 A1 | 2/2003 | Simmons |
| 2003/0048481 A1 | 3/2003 | Kobayashi |
| 2003/0050733 A1 | 3/2003 | Wang et al. |
| 2003/0060808 A1 | 3/2003 | Wilk |
| 2003/0100892 A1 | 5/2003 | Morley et al. |
| 2003/0114962 A1 | 6/2003 | Niemeyer |
| 2003/0135203 A1 | 7/2003 | Wang et al. |
| 2003/0144579 A1 | 7/2003 | Buss |
| 2003/0144649 A1 | 7/2003 | Ghodoussi et al. |

| | | | |
|---|---|---|---|
| 2003/0151658 A1 | 8/2003 | Smith | |
| 2003/0199000 A1 | 10/2003 | Valkirs et al. | |
| 2003/0220541 A1 | 11/2003 | Salisbury et al. | |
| 2003/0232649 A1* | 12/2003 | Gizis et al. | 463/40 |
| 2004/0012362 A1* | 1/2004 | Tsurumi | 318/568.12 |
| 2004/0013295 A1* | 1/2004 | Sabe et al. | 382/153 |
| 2004/0019406 A1* | 1/2004 | Wang et al. | 700/231 |
| 2004/0065073 A1 | 4/2004 | Nash | |
| 2004/0068657 A1 | 4/2004 | Alexander et al. | |
| 2004/0078219 A1 | 4/2004 | Kaylor et al. | |
| 2004/0088077 A1 | 5/2004 | Jouppi et al. | |
| 2004/0093409 A1 | 5/2004 | Thompson et al. | |
| 2004/0098167 A1 | 5/2004 | Yi et al. | |
| 2004/0117065 A1 | 6/2004 | Wang et al. | |
| 2004/0138547 A1 | 7/2004 | Wang et al. | |
| 2004/0143421 A1 | 7/2004 | Wang et al. | |
| 2004/0157612 A1 | 8/2004 | Kim | |
| 2004/0162637 A1 | 8/2004 | Wang et al. | |
| 2004/0167666 A1 | 8/2004 | Wang et al. | |
| 2004/0167668 A1 | 8/2004 | Wang et al. | |
| 2004/0174129 A1 | 9/2004 | Wang et al. | |
| 2004/0179714 A1 | 9/2004 | Jouppi | |
| 2004/0215490 A1 | 10/2004 | Duchon et al. | |
| 2004/0230340 A1* | 11/2004 | Fukuchi et al. | 700/245 |
| 2005/0003330 A1 | 1/2005 | Asgarinejad | |
| 2005/0021309 A1 | 1/2005 | Alexander et al. | |
| 2005/0024485 A1 | 2/2005 | Castles et al. | |
| 2005/0027794 A1 | 2/2005 | Decker | |
| 2005/0028221 A1 | 2/2005 | Liu et al. | |
| 2005/0035862 A1 | 2/2005 | Wildman et al. | |
| 2005/0065659 A1 | 3/2005 | Tanaka et al. | |
| 2005/0110867 A1 | 5/2005 | Schulz | |
| 2005/0192721 A1* | 9/2005 | Jouppi | 701/24 |
| 2006/0013488 A1 | 1/2006 | Inoue | |
| 2006/0142983 A1 | 6/2006 | Sorensen | |
| 2006/0161303 A1 | 7/2006 | Wang et al. | |
| 2009/0125147 A1* | 5/2009 | Wang et al. | 700/264 |

FOREIGN PATENT DOCUMENTS

| | | |
|---|---|---|
| EP | 0981905 B1 | 1/2002 |
| EP | 1 262 142 A2 | 12/2002 |
| EP | 1 536 660 B2 | 9/2004 |
| EP | 1 533 660 A2 | 6/2005 |
| JP | 2007-213753 A | 8/1995 |
| JP | 2007-248823 A | 8/1995 |
| JP | 07257422 A | 10/1995 |
| JP | 08-084328 A | 3/1996 |
| JP | 9-267276 A | 10/1997 |
| JP | 2000-032319 A | 1/2000 |
| JP | 2000-235423 A | 8/2000 |
| JP | 2001-147718 A | 5/2001 |
| JP | 2001-198865 A | 7/2001 |
| JP | 2001-198868 A | 7/2001 |
| JP | 2001-199356 A | 7/2001 |
| JP | 2000-188124 | 1/2002 |
| JP | 2002-000574 A | 1/2002 |
| JP | 2002-046088 | 2/2002 |
| JP | 2002305743 A | 10/2002 |
| JP | 2002-355779 A | 12/2002 |
| WO | WO 93/06690 A1 | 4/1993 |
| WO | WO 98/51078 A | 11/1998 |
| WO | WO 99/67067 A1 | 12/1999 |
| WO | WO 03/077745 A | 9/2003 |
| WO | WO 2004/075456 A2 | 9/2004 |

OTHER PUBLICATIONS

Baltus et al., "Towards Personal Service Robots for the Elderly", Computer Science and Robotoics.

Bauer, Jeffrey C., "Service Robots in Health Care: The Evolution of Mechanical Solutions to Human Resource Problems", Jun. 2003.

Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.

Celi et al., "The eICU: It's not just telemedicine", Critical Care Medicine, vol. 29, No. 8 (Supplement), Aug. 2001.

CNN.com/Technology, Paging R.Robot: Machine helps doctors with patients, Sep. 30, 2003, Internet, 1-3.

Davies, "Robotics in Minimally Invasive Surgery", 1995, Internet, pp. 5/1-5/2.

Ellison et al., "Telerounding and Patient Satisfaction Following Surgery".

Goldman, Lea, "Machine Dreams", Entrepreneurs, Forbes, May 27, 2002.

Harmo et al., "Moving Eye—Interactive Telepresence Over Internet With a Ball Shaped Mobile Robot", 2000.

Hees, William P., "Communications Design for a Remote Presence Robot", Jan. 14, 2002.

Jouppi, et al., :Mutually-Immersive Audio Telepresence, Audio Engineering Society Convention Paper, presented at 113th Convention Oct. 2002.

Jouppi, Norman P., "First Steps Towards Mutually-Immersive Mobile Telepresence", 2002.

Kanehiro, Fumio et al., Virtual Humanoid Robot Platform to Develop Controllers of Real Humanoid Robots without Porting, 2001,IEEE, pp. 3217-3276.

Kaplan et al., "An Internet Accessible Telepresence".

Kuzuoka et al., "Can The GestureCam Be A Surrogate?".

Lim, Hun-ok et al., Control to Realize Human-like Walking of a Biped Humanoid Robot, III 2000, pp. 3271-3276.

Loeb, Gerald, "Virtual Visit: Improving Communication for Those Who Need It Most", 2001.

Mack, "Minimally invasive and robotic surgery", 2001, IEEE, pp. 568-572.

Magne Charge—Smart Power for Electric Vehicles, Internet, Jun. 27, 2002.

Martin, Anya, "Days Ahead", Assisted Living Today, vol. 9, Nov./Dec. 2002, pp. 19-22.

McCardle et al., "The challenge of utilizing new technology in design education", 2000 Internet, pp. 122-127.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, Eric John, "Personal Tele-Embodiment", 2001.

Paulos, et al. , "Ubiquitous Tele-embodiment: Applications and Implications", International Journal of Human Computer Studies, Jun. 1997, vol. 46, No. 6, pp. 861-877.

Paulos, et al., "Designing Personal Tele-Embodiment", Presented at the IEEE International Conference on Robotics and Animation, Leuven, Belgium, May 20, 1998.

Pin et al., "A New Family of Omnidirectional and Holonomic Wheeled Platforms for Mobile Robots", IEEE, vol. 10, No. 4, Aug. 1994.

Roland Piquepaille's Technology Trends, How new technologies are modifying your way of life, 2003, Internet, pp. 1-2.

PYXIS HelpMate®, the Trackless Robotic Courier, Internet, 3 pgs.

"Remote Presence", p. 131-147.

Roy et al., "Towards Personal Service Robots for the Elderly", Internet, Mar. 7, 2002.

Stephenson, Gary, "Dr. Robot Tested at Hopkins", 2003, Internet, p. 1.

Stoianovici et al., "Robotic Tools for Minimally Invasive Urologic Surgery", Dec. 2002, Internet, 1-17.

Tendick et al., "Human-Machine Interfaces for Minimally Invasive Surgery", 1997, IEEE, pp. 1-6.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Urquhart, Kim, "InTouch's robotic Companion 'beams up' healthcare experts", Medical Device Daily, vol. 7, No. 39, Feb. 27, 2003, p. 1, 4.

Zorn, Benjamin G., "Ubiquitous Telepresence", http://www.cs.colorado.edu/~zorn/ut/vision/vision.html, Mar. 5, 1996.

Al-Kassab, "A Review of Telemedicine", Journal of Telemedicine and Telecare, 1999, vol. 5, Supplement 1.

F. Ando et al., "A Multimedia Self-service Terminal with Conferencing Functions", 1995, IEEE, pp. 357-362.

Android Amusement Corp., "What Marketing Secret . . . Renting Robots from Android Amusement Corp!", (Advertisement) 1982.

Applebome, "Planning Domesticated Robots for Tomorrow's Household", New York Times, Mar. 4, 1982, pp. 21 and 23, http://www.theoldrobots.com/images17/dc17.JPG.

Bar-Cohen et al., Virtual reality robotic telesurgery simulations using MEMICA haptic system, Mar. 5, 2001, Internet, pp. 1-7.

Bartholomew, "An Apothecary's Pharmacy", 1230-1240 http://classes.bnf.fr/ema/grands/034.htm.

Bauer, John et al., "Remote telesurgical mentoring: feasibility and efficacy", 2000, IEEE, pp. 1-9.

Bischoff, "Design Concept and Realization of the Humanoid Service Robot HERMES", Field and Service Robotics, Springer, London, 1998, pp. 485-492.

Blackwell, Gerry, "Video: A Wireless LAN Killer App?", Apr. 16, 2002, Internet pp. 1-3.

Cheetham, Anastasia et al., "Interface Development for a Child's Video Conferencing Robot", 2000, pp. 1-4.

Cleary et al., "State of the art in surgical robotics: Clinical applications and technology challenges", Feb. 24, 2002 Internet, pp. 1-26.

CNN, "Floating 'droids' to roam space corridors of the future", Jan. 12, 2000, Internet, pp. 1-4.

Crowley, "Hello to Our Future", AARP Bulletin, Jan. 2000 http://www.cs.cmu.ed/-nursebot/web/press/aarp_99_14/millennium.html.

Dalton, "Techniques for Web Telerobotics", PhD Thesis, University of Western Australia, 2001, pp. 27-62, 149-191; http://telerobot.mech.uwa.edu.au/information.html, http://catalogue.library.uwa.edu.au/search.

Discovery Channel Canada, "Inventing the Future: 2000 Years of Discovery", Jan. 2, 2000 (Video/Transcript).

Elhajj et al., "Supermedia in Internet-based telerobotic operations", 2001, Internet, pp. 1-14.

Elhajj et al., "Synchronization and Control of Supermedia Transmission Via the Internet", Proceedings of 2001 International Symposium on Intelligent Multimedia, Video and Speech Processing, May 2-4, 2001, Hong Kong.

Fels, "Developing a Video-Mediated Communication System for Hospitalized Children", Telemedicine Journal, vol. 5, No. 2, 1999.

Fetterman, "Videoconferencing over the Internet", 2001, Internet, pp. 1-8.

Fiorini, "Health Care Robotics: A Progress Report", IEEE International Conference on Robotics and Automation, pp. 1271-1276, Apr. 1997.

Ghiasi, "A Generic Web-based Teleoperations Architecture: Details and Experience", SPIE Conference on Telemanipulator and Telepresence Technologies VI, Sep. 1999.

Goldberg et al., "Collaborative Teleoperation via the Internet", IEEE International Conference on Robotics and Automation, Apr. 2000, San Francisco, California.

Goldberg, "Desktop Teleoperation via the World Wide Web, Proceedings of the IEEE International Conference on Robotics and Automation", 1995, pp. 654-659 http://citeseer.ist.psu.edu/cache/papers/cs/5/ftp:zSzzSzusc.eduzSzpubzSziriszSzraiders.pdf/gol.

Goldberg, "More Online Robots, Robots that Manipulate", Internet, Updated Aug. 2001 http://ford/ieor.berkeley.edu/ir/robots_a2.html.

Gump, Michael D., "Robot Technology Improves VA Pharmacies", 2001, Internet, pp. 1-3.

Handley, "RFC 2327—SDP: Session Description Protocol", Apr. 1998 http://www.faqs.org/rfcs/rfc2327.html.

Hanebeck, "Roman: a mobile Robotic Assistant for Indoor Service Applications", Proceedings of the 1997 IEEE/RSJ International Conference on Intelligent Robots and Systems, 1997.

Haule et al., "Control Scheme for Delayed Teleoperation Tasks", May 17, 1995, Proceedings of the Pacific Rim Conference on Communications, Computer and Signal Processing.

Holmberg, "Development of a Holonomic Mobile Robot for Mobile Manipulation Tasks", International Conference on Field and Service Robotics, Pittsburgh, PA, Aug. 1999.

Ishiguro, "Integrating a Perceptual Information Infrastructure with Robotic Avatars: A Framework for Tele-Existence" Proceeding of IEEE Conference on Intelligent Robots and Systems, http://www.ai.soc.i.kyoto-u.ac.jp/services/publications/99/99conf/07.pdf.

Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.

ITU, "ITU-T H.323 Packet-based multimedia communications", ITU, Feb. 1998, http://www.itu.int/rec/T-REC-H.323-199802-S/en.

Ivanova, Natali, "Master's thesis: Internet Based Interface for Control of a Mobile Robot", Department of Numerical Analysis and Computer Science.

Jenkins, "Telehealth Advancing Nursing Practice", Nursing Outlook, Mar./Apr. 2001, vol. 49, No. 2.

Johanson, "Supporting video-mediated communication over the Internet", Chalmers University of Technology, Dept of Computer Engineering, Gothenburg, Sweden, 2003.

Keller et al., "Raven Interface Project", Fall 2001 http://upclose.Irdc.pitt.edu/people/louw_assets/Raven_Slides.pps.

Khatib, "Robots in Human Environments", Proc. International Conference on Control, Automation, Robotics, and Vision, ICRACV2000, Dec. 2000, Singapore, pp. 454-457.

Lane, "Automated Aides", Newsday, Oct. 17, 2000, http://www.cs.cum.edu/-nursebot/web/press/nd4380.htm.

Lee et al., "A novel method of surgical instruction: International telementoring", 1998, Internet pp. 1-4.

Linebarger, John M. et al., "Concurrency Control Mechanisms for Closely Coupled Collaboration in Multithreaded Virtual Environments", Presence, Special Issue on Advances in Collaborative VEs (2004).

Long, "HelpMate Robotics, Inc. (Formerly Transitions Research Corporation) Robot Navigation Technology", NIST Special Publication 950-1, Mar. 1999, http://www.atp.nist.gov/eao/sp950-1/helpmate.htm.

Luna, Nancy, "Robot a new face on geriatric care", OC Register, Aug. 6, 2003.

Mair, "Telepresence—The Technology And Its Economic and Social Implications", IEEE Technology and Society, 1997.

Meng et al., "E-Service Robot in Home Healthcare", Proceedings of the 2000 IEEE/RSJ, International Conference on Intelligent Robots and Systems, 2000, pp. 832-837.

Michaud, "Introducing 'Nursebot'", The Boston Globe, Sep. 11, 2001, pp. 1-5, http://www.cs.cmu.edu/nursebot/web/press/globe_3_01/index.html.

Mobile Robotics Research Group, "Mobile Robotics Research Group", 2000 Internet, pp. 1-2, Edinburgh.

Montemerlo, "Telepresence: Experiments in Next Generation Internet", CMU Robotics Institute, Oct. 20, 1998, http://www.ri.cmu.edu/creative/archives.htm (Video/Transcript).

Murphy, "Introduction to A1 Robotics", 2000.

Nakajima et al., "A Multimedia Teleteaching System sing an Electronic Whiteboard for Two-Way Communication of Motion Videos and Chalkboards", 1993, IEEE, pp. 436-441.

"National Energy Research Scientific Computing Center, Berkeley Lab's RAGE Telepresence Robot Captures R&D100 Award", Jul. 2, 2002, http://www.nersc.gov/news/newsroom/RAGE070202.php.

Nomadic Technologies, Inc., "Nomad XR4000 Hardware Manual", Mar. 1999.

Ogata et al., "Emotional Communication Robot: WAMOEBA-2R—Emotion Model and Evaluation Experiments", 1999, Internet, pp. 1-16.

Ogata et al., "Development of Emotional Communication Robot: WAMOEBA-2R—Experimental evaluation . . .", 2000 IEEE, pp. 175-180.

Oh et al., "Autonomous Battery Recharging for Indoor Mobile Robots", Proceedings of Australian Conference on Robotics and Automation, 2000, http://users.rsise.anu.edu.au/rsl/rsl_papers/ACRA2000/Auto_Recharge_Paper.pdf.

Paulos, "Designing Personal Tele-embodiment", IEEE International Conference on Robotics and Automation, 1998, http://www.prop.org/papers/icra98.pdf.

Paulos, Video of PRoP 2 at Richmond Field Station, www.prop.org. May 2001, Printout of Home Page of Website and two-page Transcript of the audio portion of said PRoP Video.

Rovetta et al., "A New Telerobotic Application: Remote Laparoscopic Surgery Using Satellites and Optical Fiber Networks for Data Exchange", Jun. 1, 1996, International Journal of Robotics Research, pp. 267-279.

Sandt, Frederic et al., "Perceptions for a Transport Robot in Public Environments", 1997, IROS '97.

Schaeffer, "Care-O-bot: A System for Assisting Elderly or Disabled Persons in Home Environments", Proceedings of AAATE-99, 1999, http://morpha.de/download/publications/IPA_Systems_For_AssistingElderly_or_DisabledPersons_AAATE1999.pdf.

Schulz, "Web Interfaces for Mobile Robots in Public Places", Robotics & Automation Magazine, IEEE, vol. 7, Issue 1, Mar. 2000.

Shimoga et al., Touch and force reflection for telepresence surgery, 1994, IEEE, pp. 1049-1050.

Siegwart, "Interacting Mobile Robots on the Web", Proceedings of the 1999 IEEE International Conference on Robotics and Automation, May 1999.

Simmons, "Xavier: An Autonomous Mobile Robot on the Web", IEEE Robotics and Automation Magazine, 1999, pp. 43-48.

Spawar Systems Center, "Robart", 1998, San Diego, CA, http://web.archive.org/web/*/http://www.nosc.mil/robots/land/robart/robart.html http://web.archive.org/web/19981202205636/http://www.nosc.mil/robots/land/robart/robart.html.

Suplee, "Mastering the Robot", The Washington Post, p. A01, Sep. 17, 2000 http://www.cs.cmu.edu-nursebot/web/press/wash/index.html.

Tahboub, Karim A. et al., "Dynamics Analysis and Control of a Holonomic Vehicle With Continously Variable Transmission", Mar. 2002, Journal of Dynamic Systems, Measurement, and Control, ASME vol. 124, pp. 118-126.

Weiss et al., Telework and video-mediated communication: Importance of real-time, interactive communication for workers with disabilities, pp. 1-4, California State University Northridge, http://www.csun.edu/cod/conf/1999/proceedings/session0238.html.

West et al., "Design of Ball Wheel Mechanisms for Omnidirectional Vehicles with Full Mobility and Invariant Kinematics", Journal of Mechanical Design, vol. 119, pp. 153-161, Jun. 1997.

Yamasaki et al., Applying Personal Robots and Active Interface to Video Conference Systems, 1995, Internet, pp. 243-248.

Yamauchi et al., PackBot: A Versatile Platform for Military Robotics, 2004, Internet, pp. 1-10.

Yong et al., "Robot task execution with telepresence using virtual reality technology", 1998, Internet, pp. 1-9.

Zamrazil, Kristie, "Telemedicine in Texas: Public Policy Concerns", House Research Organization Focus Report, Texas House of Representatives, No. 76-22, May 5, 2000 http://www.hro.house.state.tx.us/focus/telemed.pdf.

Zipperer, Lorri, "Robotic dispensing system", 1999, Internet, pp. 1-2.

* cited by examiner

MOBILE ROBOT WITH A HEAD-BASED MOVEMENT MAPPING SCHEME

BACKGROUND OF THE INVENTION

1. Field of the Invention

The subject matter disclosed generally relates to the field of robotics.

2. Background Information

There is a growing need to provide remote health care to patients that have a variety of ailments ranging from Alzheimers to stress disorders. To minimize costs it is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel.

The assignee of this invention(s), InTouch-Health, Inc. markets a remote controlled mobile robot under the trademark COMPANION that can be used by medical personnel to remotely "visit" patients. The COMPANION system includes a mobile robot with a camera, monitor, microphone, speakers, and other equipment that allow for two-way audio/visual communication between the patient and someone operating the system from a remotely located computer.

The COMPANION system includes a joystick that can be manipulated to move a mobile platform of the robot. A forward pivot of the joystick causes a corresponding forward movement of the mobile platform. The joystick button can be depressed to move the camera and allow the user to pan a room. Unfortunately, panning the camera may cause the forward viewing direction depicted by the screen to be different than the forward vector of the mobile platform. A forward pivot of the joystick will cause an angular movement of the robot relative to the field of view provided by the robot camera. This can cause disorientation and in general complicates movement of the robot.

BRIEF SUMMARY OF THE INVENTION

A mobile robot system that is controlled through an input device. The system includes a robot that has a camera located in a camera reference coordinate system, and a mobile platform. The input device causes movement of the camera, and movement of the mobile platform within the camera reference coordinate system.

DETAILED DESCRIPTION

Disclosed is a robotic system that includes a mobile robot and a remote input device. The input device may be a joystick that is used to move a camera and a mobile platform of the robot. The system may operate in a mode where the mobile platform moves in a camera reference coordinate system. The camera reference coordinate system is fixed to a viewing image provided by the camera so that movement of the robot corresponds to a direction viewed on a screen. This prevents disorientation during movement of the robot if the camera is panned across a viewing area.

Figure 1:
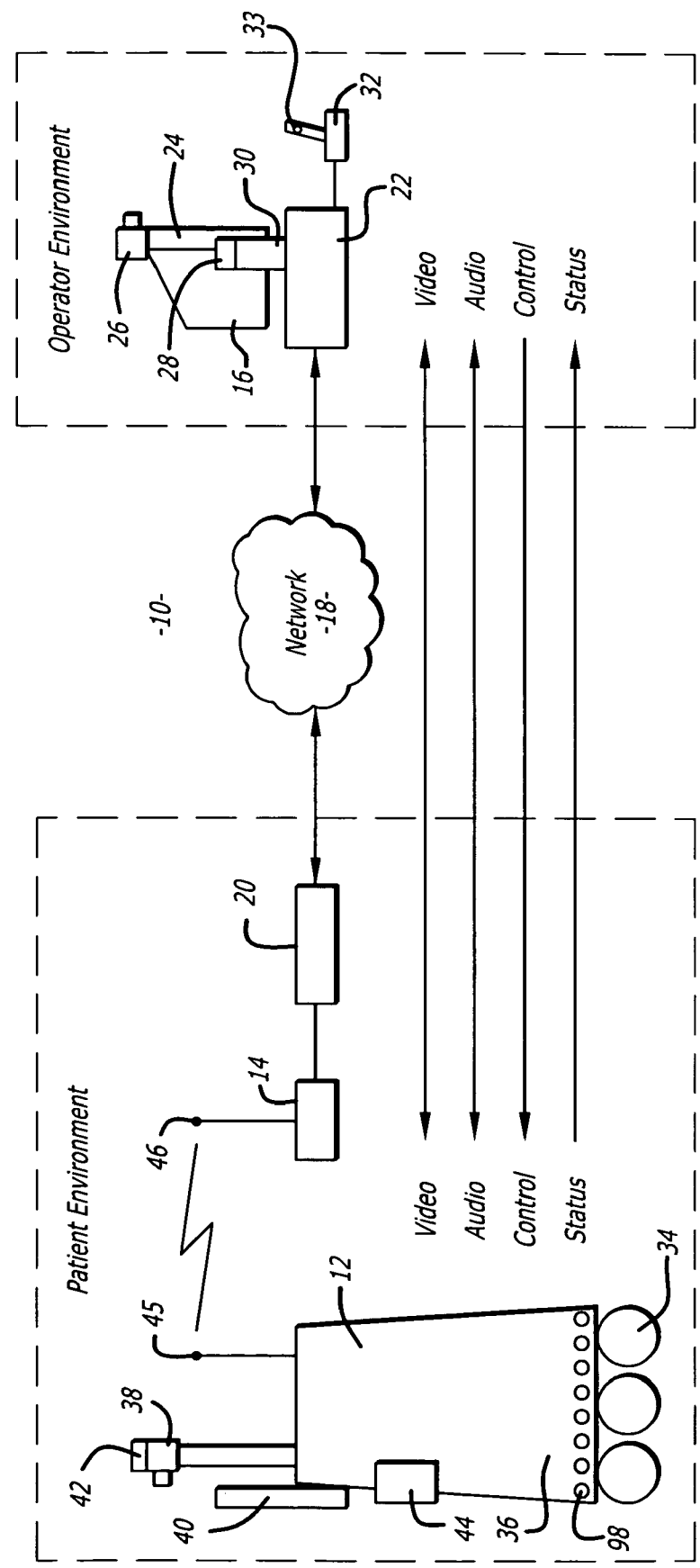
FIG. 1 is an illustration of a robotic system.

Referring to the drawings more particularly by reference numbers, FIG. 1 shows a robotic system 10. The robotic system 10 includes a robot 12, a base station 14 and a remote control station 16. The remote control station 16 may be coupled to the base station 14 through a network 18. By way of example, the network 18 may be either a packet switched network such as the Internet, or a circuit switched network such has a Public Switched Telephone Network (PSTN), or other broadband system. The base station 14 may be coupled to the network 18 by a modem 20 or other broadband network interface device.

The remote control station 16 may include a computer 22 that has a monitor 24, a camera 26, a microphone 28 and a speaker 30. The computer 22 may also contain an input device 32 such as a joystick or a mouse. The joystick 32 may have a toggle button 33 that allows the system to operate in two different modes. In one mode the robot moves in a platform reference coordinate system. In another mode the robot moves in a camera reference coordinate system.

The control station 16 is typically located in a place that is remote from the robot 12. Although only one robot 12 and one station 16 are shown, it is to be understood that the system 10 may have a plurality of robots 12 and/or a plurality of remote stations that communicate through the broadband network. In general any number of robots 12 may be controlled by any number of remote stations 16. For example, one remote station 16 may be coupled to a plurality of robots 12, or one robot 12 may be coupled to a plurality of remote stations 16.

The robot 12 includes a mobile platform 34 that is attached to a robot housing 36. Also attached to the robot housing 36 are a camera 38, a monitor 40, a microphone(s) 42 and a speaker 44. The microphone 42 and speaker 30 may create a stereophonic sound. The robot 12 may also have an antenna 45 that is wirelessly coupled to an antenna 46 of the base station 14. The system 10 allows a user at the remote control station 16 to move the robot 12 through the input device 32. The robot camera 38 is coupled to the remote monitor 24 so that a user at the remote station 16 can view a patient. Likewise, the robot monitor 40 is coupled to the remote camera 26 so that the patient can view the user. The microphones 28 and 42, and speakers 30 and 44, allow for audible communication between the patient and the user.

Each remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

Figure 2:
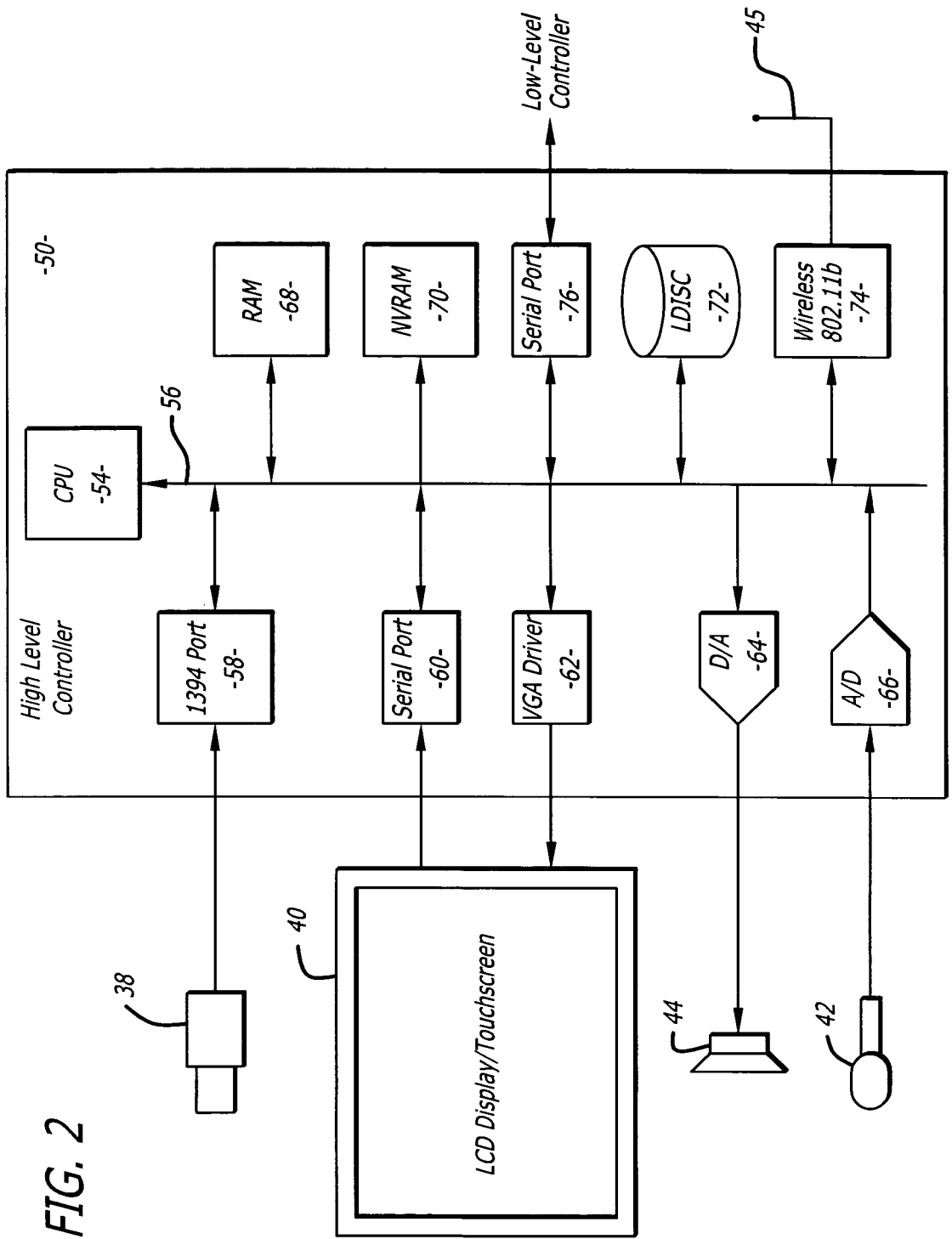
FIG. 2 is a schematic of an electrical system of a robot.
Figure 3:
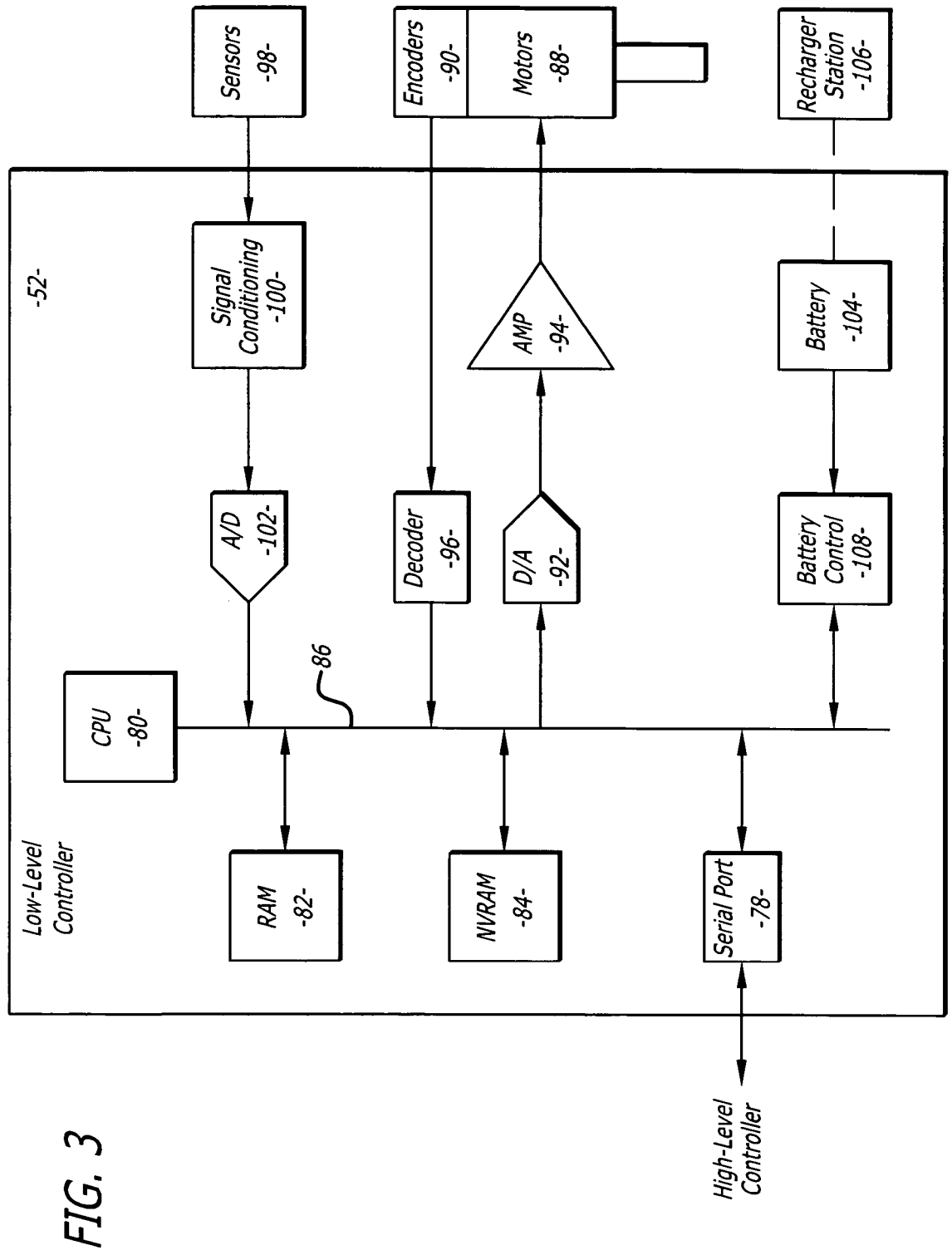
FIG. 3 is a further schematic of the electrical system of the robot.

FIGS. 2 and 3 show an embodiment of the robot 12. The robot 12 may include a high level control system 50 and a low level control system 52. The high level control system 50 may include a processor 54 that is connected to a bus 56. The bus is coupled to the camera 38 by an input/output (I/O) port 58, and to the monitor 40 by a serial output port 60 and a VGA driver 62. The monitor 40 may include a touchscreen function that allows the patient to enter input by touching the monitor screen.

The speaker 44 is coupled to the bus 56 by a digital to analog converter 64. The microphone 42 is coupled to the bus 56 by an analog to digital converter 66. The high level controller 50 may also contain random access memory (RAM) device 68, a non-volatile RAM device 70 and a mass storage device 72 that are all coupled to the bus 62. The mass storage device 72 may contain medical files of the patient that can be accessed by the user at the remote control station 16. For example, the mass storage device 72 may contain a picture of the patient. The user, particularly a health care provider, can recall the old picture and make a side by side comparison on the monitor 24 with a present video image of the patient provided by the camera 38. The robot antennae 45 may be coupled to a wireless transceiver 74. By way of example, the transceiver 74 may transmit and receive information in accordance with IEEE 802.11b.

The controller 54 may operate with a LINUX OS operating system. The controller 54 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 50 operates to control the communication between the robot 12 and the remote control station 16.

The high level controller 50 may be linked to the low level controller 52 by serial ports 76 and 78. The low level controller 52 includes a processor 80 that is coupled to a RAM device 82 and non-volatile RAM device 84 by a bus 86. The robot 12 contains a plurality of motors 88 and motor encoders 90. The encoders 90 provide feedback information regarding the output of the motors 88. The motors 88 can be coupled to the bus 86 by a digital to analog converter 92 and a driver amplifier 94. The encoders 90 can be coupled to the bus 86 by a decoder 96. The robot 12 also has a number of proximity sensors 98 (see also FIG. 1). The position sensors 98 can be coupled to the bus 86 by a signal conditioning circuit 100 and an analog to digital converter 102.

The low level controller 52 runs software routines that mechanically actuate the robot 12. For example, the low level controller 52 provides instructions to actuate the movement platform to move the robot 12. The low level controller 52 may receive movement instructions from the high level controller 50. The movement instructions may be received as movement commands from the remote control station 16. Although two controllers are shown, it is to be understood that the robot 12 may have one controller controlling the high and low level functions.

The various electrical devices of the robot 12 may be powered by a battery(ies) 104. The battery 104 may be recharged by a battery recharger station 106 (see also FIG. 1). The low level controller 52 may include a battery control circuit 108 that senses the power level of the battery 104. The low level controller 52 can sense when the power falls below a threshold and then send a message to the high level controller 50. The high level controller 50 may include a power management software routine that causes the robot 12 to move so that the battery 104 is coupled to the recharger 106 when the battery power falls below a threshold value. Alternatively, the user can direct the robot 12 to the battery recharger 106. Additionally, the battery 104 may be replaced or the robot 12 may be coupled to a wall power outlet by an electrical cord (not shown).

Figure 4:
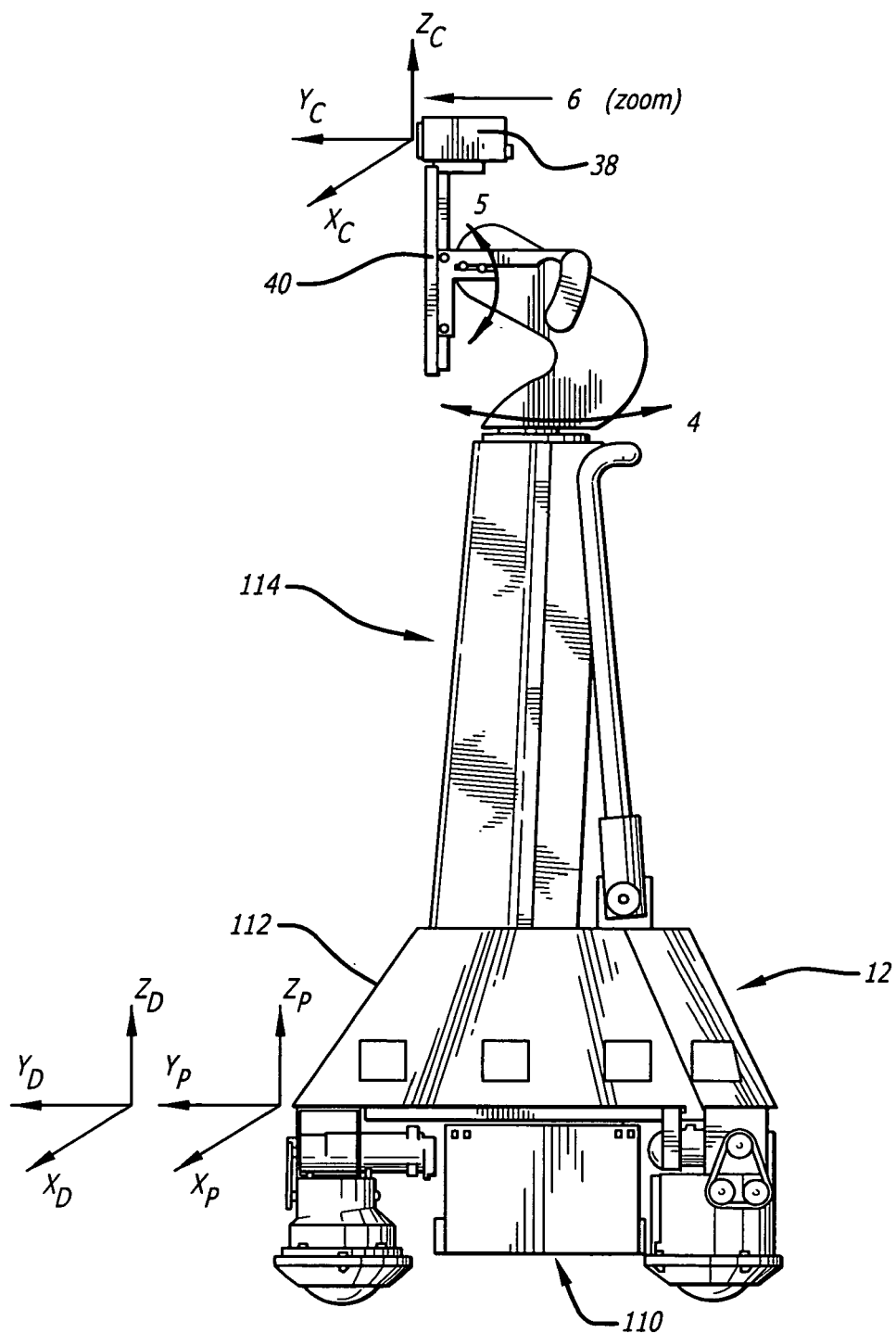
FIG. 4 is side view of the robot.

FIG. 4 shows an embodiment of the robot 12. The robot 12 may include a holonomic platform 110 that is attached to a robot housing 112. The holonomic platform 110 provides three degrees of freedom to allow the robot 12 to move in any direction.

The robot 12 may have a pedestal assembly 114 that supports the camera 38 and the monitor 40. The pedestal assembly 114 may have two degrees of freedom so that the camera 26 and monitor 24 can be swiveled and pivoted as indicated by the arrows.

The platform 110 is located within a platform reference coordinate system that may have axes $X_p$, $Y_p$ and $Z_p$. By way of example, the y-axis $Y_p$ may extend from a nose of the platform 110. The camera 38 is fixed to a camera reference coordinate system that may have axes $X_c$, $Y_c$ and $Z_c$. The y-axis $Y_c$ may extend perpendicular from the camera lens. When the robot is initialized, the y-axis $Y_c$ of the camera coordinate system may be aligned with the y-axis $Y_p$ of the platform coordinate system. A forward pivoting of the joystick 32 (shown in FIG. 1) may cause a corresponding movement of the platform 110 in the direction of the y-axis $Y_p$ in the platform coordinate system.

The robot may have a drive vector that may have axes $X_d$, $Y_d$, and $Z_d$ that is mapped to the camera coordinate system, the platform coordinate system or some other system. By way of example, the y-axis $Y_p$ may extend in the direction of forward motion. Mapping includes the process of transforming an input command into a directional movement relative to one or more coordinate systems. The robot controller may perform certain algorithms to translate input commands to platform movement in accordance with a specified mapping scheme. For example, when the drive vector is mapped to the camera coordinate system the controller computes the drive vector of the input command relative to the camera coordinate system. In a platform mapping scheme the input drive vector is computed relative to the platform coordinate system. In yet another scheme the drive vector can be computed relative to another coordinate system, such as a world coordinate system (e.g. coordinate system relative to the ground) that is independent of the camera or platform coordinate systems. Mapping the drive vector to the camera coordinate system may be desirable because all movement would be relative to the image viewed by the user, providing a system that is intuitive to use.

A twisting of the joystick 32 may cause the camera 38 to swivel as indicated by arrows 4. For example, if the joystick 32 is twisted +45 degrees the camera 38 will pivot +45 degrees. Swiveling the camera 38 also moves the y-axis $Y_c$ of the camera coordinate system, because the y-axis $Y_c$ is fixed to the camera. This may be different than the drive direction. The remote station computer may operate a program to generate a command that will automatically rotate the platform 110 to realign the y-axis $Y_p$ of the platform coordinate system with the y-axis $Y_c$ of the camera coordinate system. For the above example, the platform 110 is rotated +45 degrees. This approach keeps the platform 110 aligned with the camera 38, so that any subsequent movement of the robot will be intuitive relative to the image provided by the camera. For example, a forward pivot of the joystick will induce a forward movement of the robot as viewed through the monitor of the remote station. In this driving scheme, the platform may not be aligned with the head. The computer may generate trajectory planning for the platform coordinate system to move into alignment with the head coordinate system over a period of time or distance traveled, with or without an initial delay in time or some distance.

Figure 5:
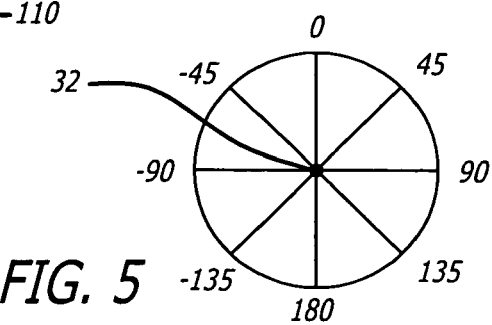
FIG. 5 is an illustration of a mapping scheme for a joystick of the system.

The system may be configured so that pivotal movement of the joystick 32 may be mapped to a corresponding directional movement of the robot as shown in FIG. 5. For example, pivoting the joystick along the +45 degree line shown in FIG. 5 may cause the robot to move in a +45 degree direction relative to the y-axis $Y_c$ of the camera coordinate frame. Alternatively, the camera may pan +45 degrees and the platform 110 may rotate +45 degrees before forward movement by the robot. The automatic panning and platform rotation causes the robot to move in a forward direction as depicted by the image provided by the camera. The robot may have a mode wherein the user can twist the joystick to pan the camera during robot movement such that the movement is not in the direction the camera is pointing. This allows the user to visually pan while moving the robot. The joystick may have a spring return that automatically returns the position of the stick when released by the user. This causes the camera to be aligned with the direction of movement.

In general the robot may have a number of different mapping schemes and relative, dependent or independent, movement between the camera, the platform and drive direction. Relative movement between the camera and platform may occur in a camera based mapping scheme, a platform based mapping scheme, or some other scheme.

Although, the automatic platform rotation commands have been described as be generated by the remote station computer, it is to be understood that the robot may determine the commands and signals necessary to re-orient the platform 110 and/or the camera 38. The robot 12 may include a potentiometer (not shown) that tracks the position of the camera and provides feedback to the low level controller 80. The low level controller 80 may automatically rotate the platform to align the y-axes $Y_c$ and $Y_p$ or otherwise compensate for camera movement. The mode button 33 may allow the operator to place the system in either a tracking mode or a normal mode. In the tracking mode the robot moves relative to the camera coordinate system so that movement is intuitive relative to the screen even when the camera is panned. In normal mode the robot moves within the platform coordinate system.

Figure 6:
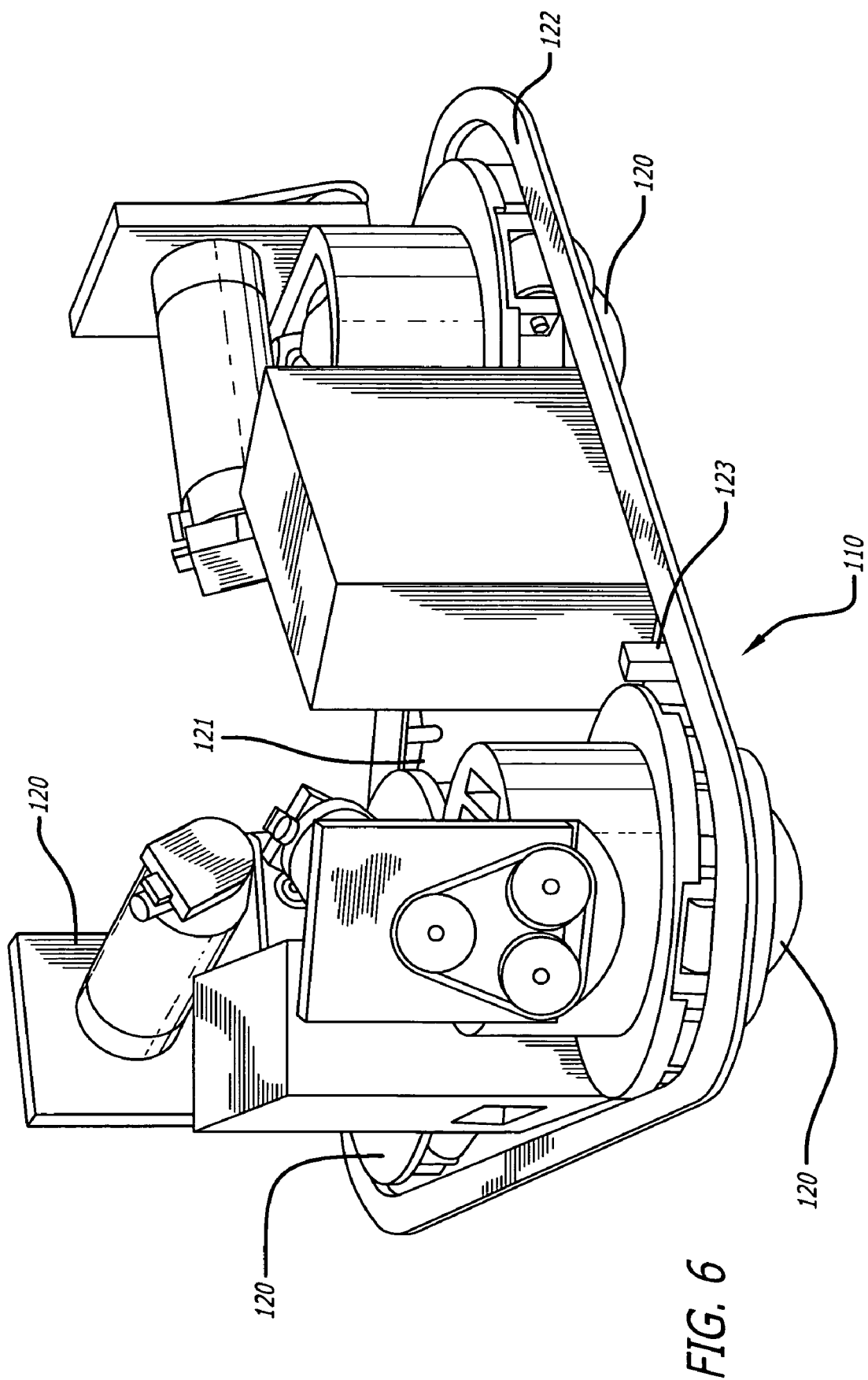
FIG. 6 is a top perspective view of a holonomic platform of the robot.

FIG. 6 shows an embodiment of a holonomic platform 110 may include three roller assemblies 120 that are mounted to a base plate 121. The roller assemblies 120 are typically equally spaced about the platform 110 and allow for movement in any direction, although it is to be understood that the assemblies may not be equally spaced.

The robot housing 112 may include a bumper 122. The bumper 122 may be coupled to optical position sensors 123 that detect when the bumper 122 has engaged an object. After engagement with the object the robot can determine the direction of contact and prevent further movement into the object.

Figure 7:
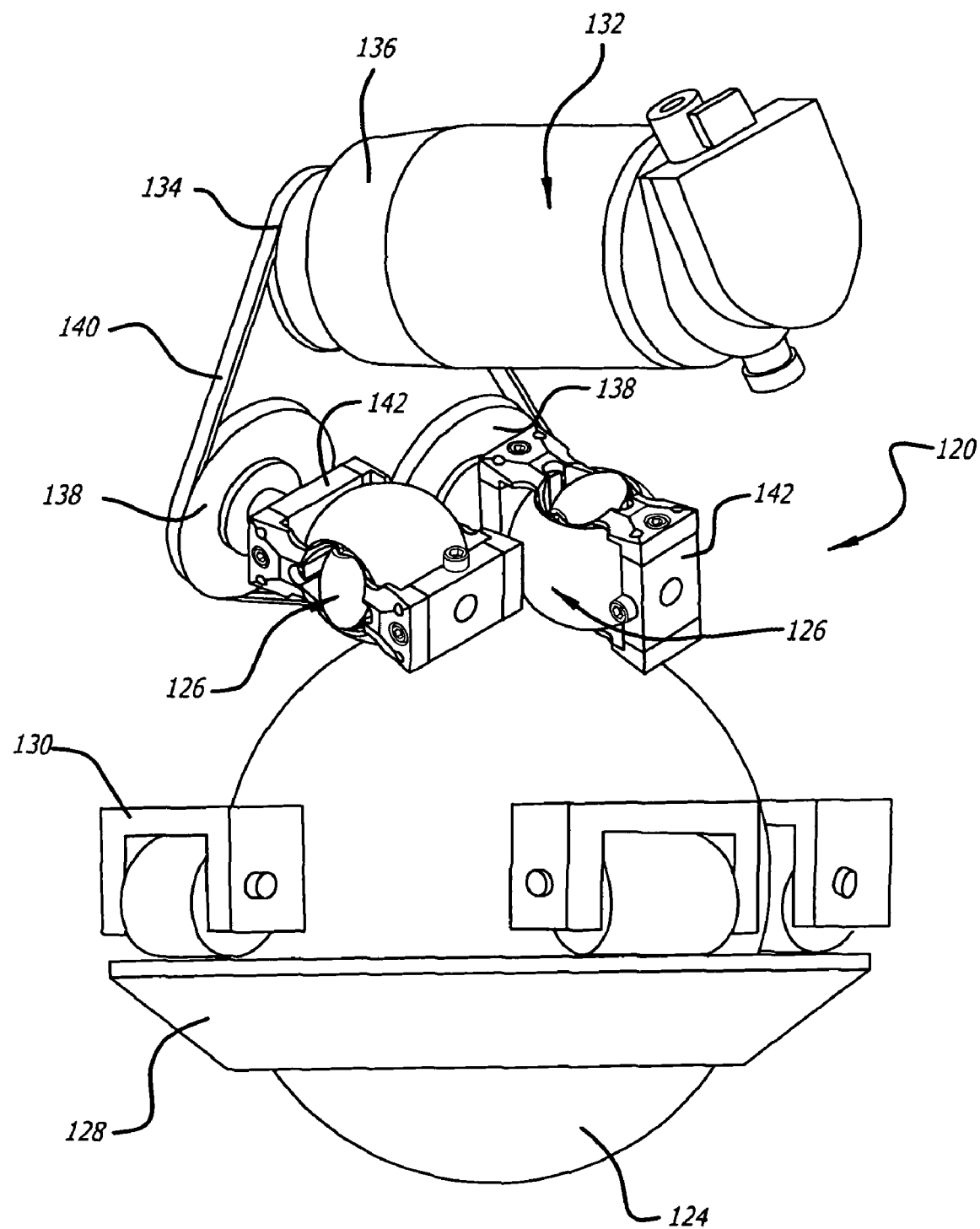
FIG. 7 is a side perspective view of a roller assembly of the holonomic platform.

FIG. 7 shows an embodiment of a roller assembly 120. Each assembly 120 may include a drive ball 124 that is driven by a pair of transmission rollers 126. The assembly 120 may include a retainer ring 128 and a plurality of bushings 130 that captures and allows the ball 124 to rotate in an x and y direction but prevents movement in a z direction. The assembly also holds the ball under the transmission rollers 126.

The transmission rollers 126 are coupled to a motor assembly 132. The assembly 132 corresponds to the motor 88 shown in FIG. 3. The motor assembly 132 includes an output pulley 134 attached to a motor 136. The output pulley 134 is coupled to a pair of ball pulleys 138 by a drive belt 140. The ball pulleys 138 are each attached to a transmission bracket 142. The transmission rollers 126 are attached to the transmission brackets 142.

Rotation of the output pulley 134 rotates the ball pulleys 138. Rotation of the ball pulleys 138 causes the transmission rollers 126 to rotate and spin the ball 124 through frictional forces. Spinning the ball 124 will move the robot 12. The transmission rollers 126 are constructed to always be in contact with the drive ball 124. The brackets 142 allow the transmission rollers 126 to freely spin in a direction orthogonal to the drive direction when one of the other roller assemblies 120 is driving and moving the robot 12.

Figure 8:
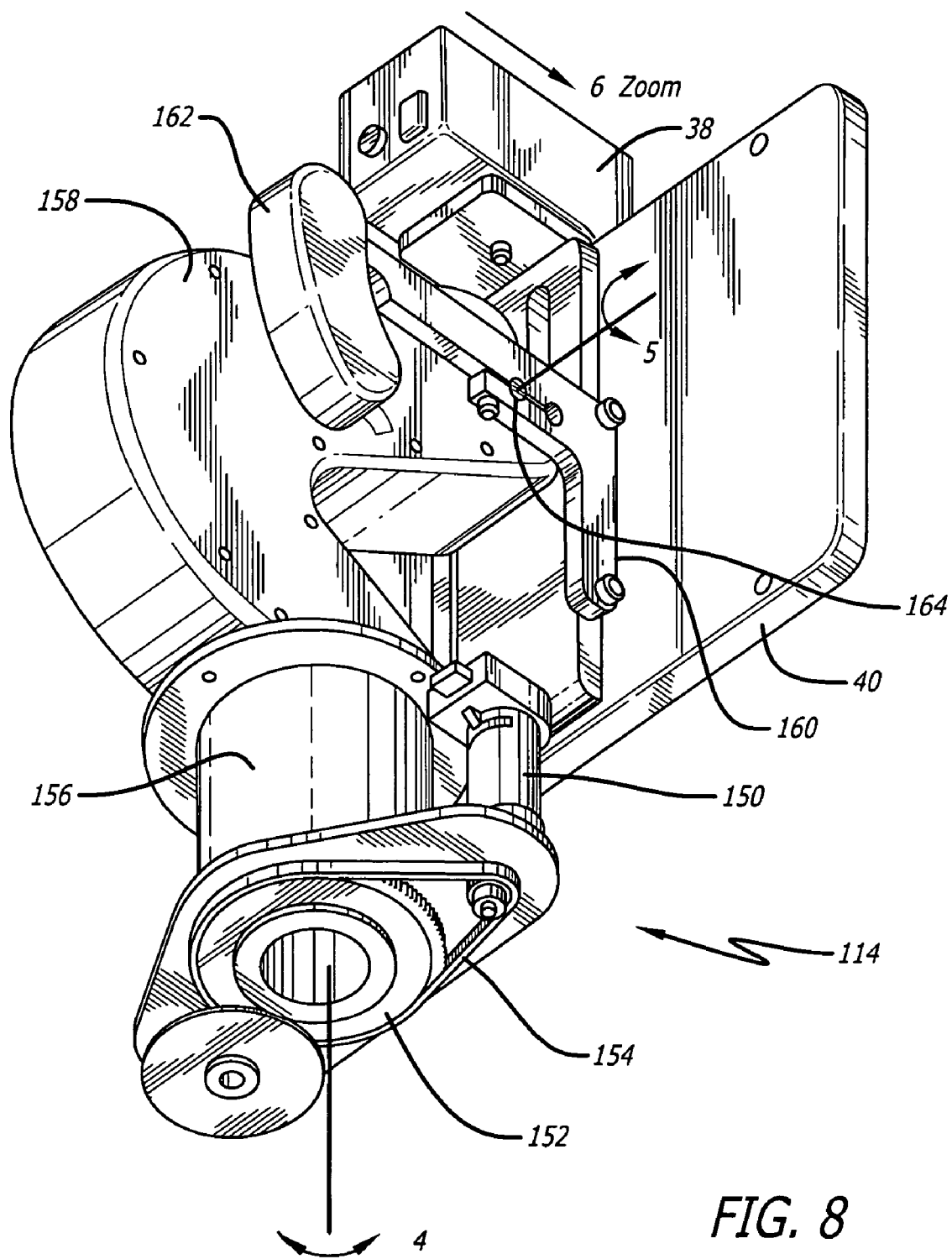
FIG. 8 is a bottom perspective view showing a pedestal assembly of the robot.

As shown in FIG. 8, the pedestal assembly 114 may include a motor 150 that is coupled to a gear 152 by a belt 154. The gear 152 is attached to a shaft 156. The shaft 156 is attached to an arm 158 that is coupled to the camera 38 and monitor 40 by a bracket 160. Activation of the motor 150 rotates the gear 152 and sleeve 156, and causes the camera 38 and monitor 40 to swivel (see also FIG. 4) as indicated by the arrows 4.

Figure 9:
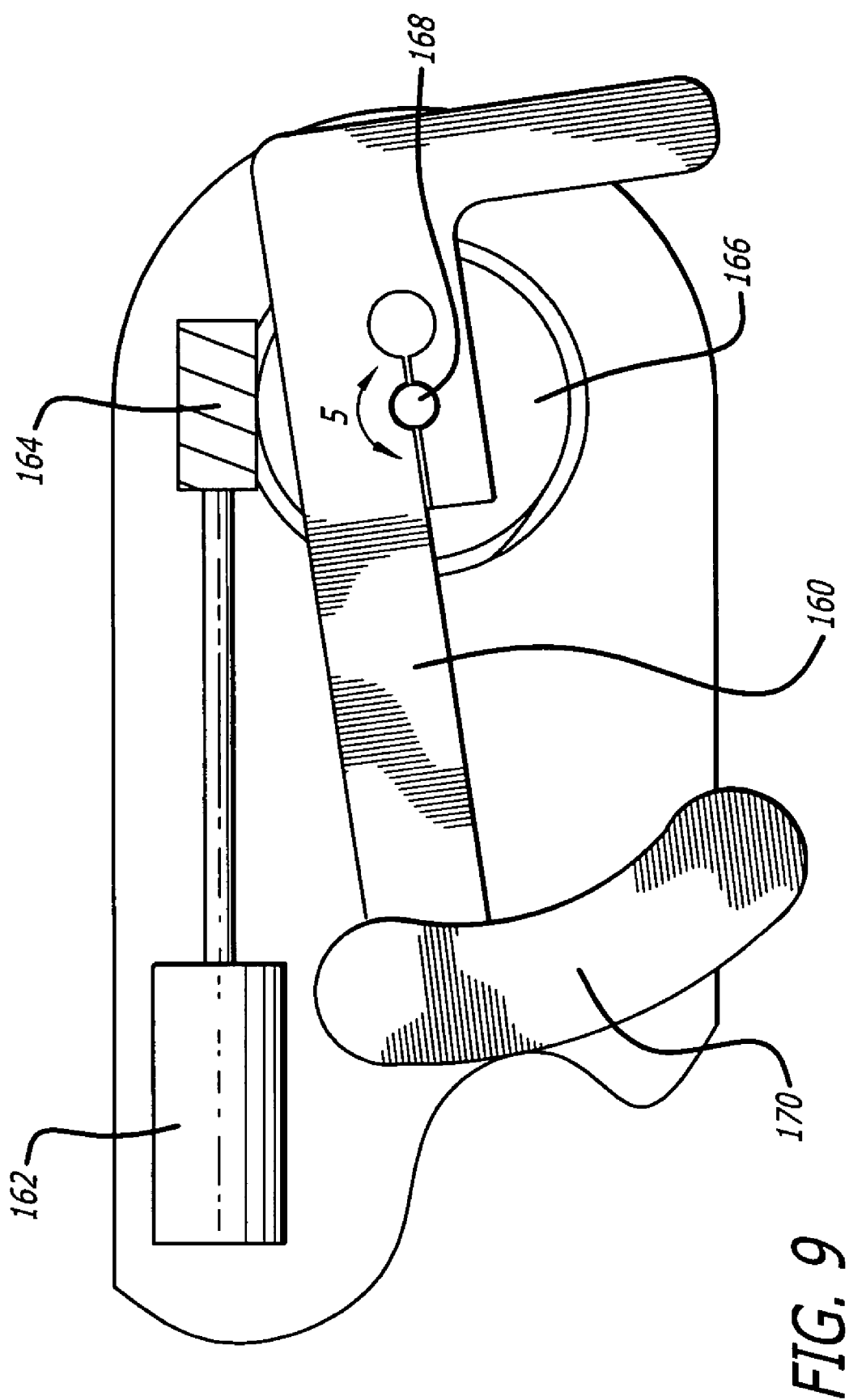
FIG. 9 is a sectional view showing an actuator of the pedestal assembly.

As shown in FIG. 9, the assembly 114 may further include a tilt motor 162 within the arm 158 that can cause the monitor 40 and camera 38 to pivot as indicated by the arrows 5. The tilt motor 162 may rotate a worm 164 that rotates a worm gear 166. The pin 168 is rigidly attached to both the worm gear 166 and the bracket 160 so that rotation of the gear 166 pivots the camera 38 and the monitor 40. The camera 38 may also include a zoom feature to provide yet another degree of freedom for the operator.

In operation, the robot 12 may be placed in a home or a facility where one or more patients are to be monitored and/or assisted. The facility may be a hospital or a residential care facility. By way of example, the robot 12 may be placed in a home where a health care provider may monitor and/or assist the patient. Likewise, a friend or family member may communicate with the patient. The cameras and monitors at both the robot and remote control stations allow for teleconferencing between the patient and the person at the remote station(s).

The robot 12 can be maneuvered through the home or facility by manipulating the input device 32 at a remote station 16. The robot 10 may be controlled by a number of different users. To accommodate for this the robot may have an arbitration system. The arbitration system may be integrated into the operating system of the robot 12. For example, the arbitration technique may be embedded into the operating system of the high-level controller 50.

By way of example, the users may be divided into classes that include the robot itself, a local user, a caregiver, a doctor, a family member, or a service provider. The robot 12 may override input commands that conflict with robot operation. For example, if the robot runs into a wall, the system may ignore all additional commands to continue in the direction of the wall. A local user is a person who is physically present with the robot. The robot could have an input device that allows local operation. For example, the robot may incorporate a voice recognition system that receives and interprets audible commands.

A caregiver is someone who remotely monitors the patient. A doctor is a medical professional who can remotely control the robot and also access medical files contained in the robot memory. The family and service users remotely access the robot. The service user may service the system such as by upgrading software, or setting operational parameters.

The robot 12 may operate in one of two different modes; an exclusive mode, or a sharing mode. In the exclusive mode only one user has access control of the robot. The exclusive mode may have a priority assigned to each type of user. By way of example, the priority may be in order of local, doctor, caregiver, family and then service user. In the sharing mode two or more users may share access with the robot. For example, a caregiver may have access to the robot, the caregiver may then enter the sharing mode to allow a doctor to also access the robot. Both the caregiver and the doctor can conduct a simultaneous teleconference with the patient.

The arbitration scheme may have one of four mechanisms; notification, timeouts, queue and call back. The notification mechanism may inform either a present user or a requesting user that another user has, or wants, access to the robot. The timeout mechanism gives certain types of users a prescribed amount of time to finish access to the robot. The queue mechanism is an orderly waiting list for access to the robot. The call back mechanism informs a user that the robot can be accessed. By way of example, a family user may receive an e-mail message that the robot is free for usage. Tables I and II, show how the mechanisms resolve access request from the various users.

TABLE I

| User | Access Control | Medical Record | Command Override | Software/Debug Access | Set Priority |
|---|---|---|---|---|---|
| Robot | No | No | Yes (1) | No | No |
| Local | No | No | Yes (2) | No | No |
| Caregiver | Yes | Yes | Yes (3) | No | No |
| Doctor | No | Yes | No | No | No |
| Family | No | No | No | No | No |
| Service | Yes | No | Yes | Yes | Yes |

TABLE II

| Current User | Requesting User | | | | |
| | Local | Caregiver | Doctor | Family | Service |
|---|---|---|---|---|---|
| Local | Not Allowed | Warn current user of pending user Notify requesting user that system is in use Set timeout | Warn current user of pending user Notify requesting user that system is in use Set timeout = 5 m | Warn current user of pending user Notify requesting user that system is in use Set timeout = 5 m Call back | Warn current user of pending user Notify requesting user that system is in use No timeout Call back |
| Caregiver | Warn current user of pending user. Notify requesting user that system is in use. Release control | Not Allowed | Warn current user of pending user Notify requesting user that system is in use Set timeout = 5 m Queue or callback | Warn current user of pending user Notify requesting user that system is in use Set timeout = 5 m | Warn current user of pending user Notify requesting user that system is in use No timeout Callback |
| Doctor | Warn current user of pending user Notify requesting user that system is in use Release control | Warn current user of pending user Notify requesting user that system is in use Set timeout = 5 m | Warn current user of pending user Notify requesting user that system is in use No timeout Callback | Notify requesting user that system is in use No timeout Queue or callback | Warn current user of pending user Notify requesting user that system is in use No timeout Callback |
| Family | Warn current user of pending user Notify requesting user that system is in use Release Control | Notify requesting user that system is in use No timeout Put in queue or callback | Warn current user of pending user Notify requesting user that system is in use Set timeout = 1 m | Warn current user of pending user Notify requesting user that system is in use Set timeout = 5 m Queue or callback | Warn current user of pending user Notify requesting user that system is in use No timeout Callback |
| Service | Warn current user of pending user Notify requesting user that system is in use No timeout | Notify requesting user that system is in use No timeout Callback | Warn current user of request Notify requesting user that system is in use No timeout Callback | Warn current user of pending user Notify requesting user that system is in use No timeout Queue or callback | Not Allowed |

The information transmitted between the station 16 and the robot 12 may be encrypted. Additionally, the user may have to enter a password to enter the system 10. A selected robot is then given an electronic key by the station 16. The robot 12 validates the key and returns another key to the station 16. The keys are used to encrypt information transmitted in the session.

The robot 12 and remote station 16 transmit commands through the broadband network 18. The commands can be generated by the user in a variety of ways. For example, commands to move the robot may be generated by moving the joystick 32 (see FIG. 1). The commands are preferably assembled into packets in accordance with TCP/IP protocol. Table III provides a list of control commands that are generated at the remote station and transmitted to the robot through the network.

TABLE III

| Control Commands | | |
|---|---|---|
| Command | Example | Description |
| drive | drive 10.0 0.0 5.0 | The drive command directs the robot to move at the specified velocity (in cm/sec) in the (x, y) plane, and turn its facing at the specified rate (degrees/sec). |
| goodbye | goodbye | The goodbye command terminates a user session and relinquishes control of the robot |
| gotoHomePosition | gotoHomePosition 1 | The gotoHomePosition command moves the head to a fixed "home" position (pan and tilt), and restores zoom to default value. The index value can be 0, 1, or 2. The exact pan/tilt values for each index are specified in robot configuration files. |
| head | head vel pan 5.0 tilt 10.0 | The head command controls the head motion. It can send commands in two modes, identified by keyword: either positional ("pos") or velocity ("vol"). In velocity mode, the pan and tilt values are desired velocities of the head on the pan and tilt axes, in degree/sec. A single command can include just the pan section, or just the tilt section, or both. |
| keepalive | keepalive | The keepalive command causes no action, but keeps the communication (socket) link open so that a session can continue. In scripts, it can be used to introduce delay time into the action. |
| odometry | odometry 5 | The odometry command enables the flow of odometry messages from the robot. The argument is the number of times odometry is to be reported each second. A value of 0 turns odometry off. |
| reboot | reboot | The reboot command causes the robot computer to reboot immediately. The ongoing session is immediately broken off. |
| restoreHeadPosition | restoreHeadPosition | The restoreHeadPosition functions like the gotoHomePosition command, but it homes the head to a position previously saved with gotoHomePosition. |
| saveHeadPosition | saveHeadPosition | The saveHeadPosition command causes the robot to save the current head position (pan and tilt) in a scratch location in temporary storage so that this position can be restored. Subsequent calls to "restoreHeadPosition" will restore this saved position. Each call to saveHeadPosition overwrites any previously saved position. |
| setCameraFocus | setCameraFocus 100.0 | The setCameraFocus command controls focus for the camera on the robot side. The value sent is passed "raw" to the video application running on the robot, which interprets it according to its own specification. |
| setCameraZoom | setCameraZoom 100.0 | The setCameraZoom command controls zoom for the camera on the robot side. The value sent is passed "raw" to the video application running on the robot, which interprets it according to its own specification. |
| shutdown | Shutdown | The shutdown command shuts down the robot and powers down its computer. |
| stop | stop | The stop command directs the robot to stop moving immediately. It is assumed this will be as sudden a stop as the mechanism can safely accommodate. |
| timing | Timing 3245629 500 | The timing message is used to estimate message latency. It holds the UCT value (seconds + milliseconds) of the time the message was sent, as recorded on the sending machine. To do a valid test, you must compare results in each direction (i.e., sending from machine A to machine B, then from machine B to machine A) in order to account for differences in the clocks between the two machines. The robot records |

TABLE III-continued

Control Commands

| Command | Example | Description |
| --- | --- | --- |
| userTask | userTask "Jane Doe" "Remote Visit" | data internally to estimate average and maximum latency over the course of a session, which it prints to log files. The userTask command notifies the robot of the current user and task. It typically is sent once at the start of the session, although it can be sent during a session if the user and/or task change. The robot uses this information for record-keeping. |

Table IV provides a list of reporting commands that are generated by the robot and transmitted to the remote station through the network.

TABLE IV

Reporting Commands

| Command | Example | Description |
| --- | --- | --- |
| abnormalExit | abnormalExit | This message informs the user that the robot software has crashed or otherwise exited abnormally. Te robot software catches top-level exceptions and generates this message if any such exceptions occur. |
| bodyType | bodyType 3 | The bodyType message informs the station which type body (using the numbering of the mechanical team) the current robot has. This allows the robot to be drawn correctly in the station user interface, and allows for any other necessary body-specific adjustments. |
| driveEnabled | driveEnabled true | This message is sent at the start of a session to indicate whether the drive system is operational. |
| emergencyShutdown | emergencyShutdown | This message informs the station that the robot software has detected a possible "runaway" condition (an failure causing the robot to move out of control) and is shutting the entire system down to prevent hazardous motion. |
| odometry | odometry 10 20 340 | The odometry command reports the current (x, y) position (cm) and body orientation (degrees) of the robot, in the original coordinate space of the robot at the start of the session. |
| sensorGroup | group_data | Sensors on the robot are arranged into groups, each group of a single type (bumps, range sensors, charge meter, etc.) The sensorGroup message is sent once per group at the start of each session. It contains the number, type, locations, and any other relevant data for the sensors in that group. The station assumes nothing about the equipment carried on the robot; everything it knows about the sensors comes from the sensorGroup messages. |
| sensorState | groupName state data | The sensorState command reports the current state values for a specified group of sensor. The syntax and interpretation for the state data is specific to each group. This message is sent once for each group at each sensor evaluation (normally several times per second). |
| systemError | systemError driveController | This message informs the station user of a failure in one of the robot's subsystems. The error_type argument indicates which subsystem failed, including driveController, sensorController, headHome. |
| systemInfo | systemInfo wireless 45 | This message allows regular reporting of information that falls outside the sensor system such as wireless signal strength. |

TABLE IV-continued

Reporting Commands

| Command | Example | Description |
| --- | --- | --- |
| text | text "This is some text" | The text string sends a text string from the robot to the station, where the string is displayed to the user. This message is used mainly for debugging. |
| version | version 1.6 | This message identifies the software version currently running on the robot. It is sent once at the start of the session to allow the station to do any necessary backward compatibility adjustments. |

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A mobile robot system that is controlled through an input device, comprising:
a robot that has a camera located in a camera coordinate system that has at least a first camera axis and a mobile platform located within platform coordinate system that has at least a first platform axis; and,
an input device that can be manipulated to cause said robot to move in at least three directions, each direction causes linear movement of said mobile platform in a drive direction without first rotating said mobile platform, said robot automatically moves and aligns said camera and said mobile platform while said robot is moving such that the first camera axis of the camera coordinate system is aligned with a first platform axis of the platform coordinate system from a state wherein said first camera and said first mobile platform axes were not in alignment.

2. The system of claim 1, wherein said input device is a joystick.

3. The system of claim 2, wherein twisting said joystick causes rotation of said camera and pivoting said joystick causes said mobile platform to move.

4. The system of claim 1, further comprising a remote control station with a camera coupled to a monitor of said robot.

5. A method for controlling a robot, comprising:
providing a robot that has a camera, the camera being located in a camera coordinate system with at least a first camera axis and the mobile platform being located in a platform system with at least a first platform axis;
providing an input device that can be manipulated to cause robot movement in at least three directions;
moving the camera such that said first camera axis is not aligned with said first platform axis; and
moving the robot and automatically aligning the camera and mobile platform while the robot is moving so that the first camera axis of the camera coordinate system is aligned with the first platform axis of the platform coordinate system.

* * * * *

UNITED STATES PATENT AND TRADEMARK OFFICE
CERTIFICATE OF CORRECTION

PATENT NO.        : 8,077,963 B2
APPLICATION NO.   : 10/890891
DATED             : December 13, 2011
INVENTOR(S)       : Yulun Wang et al.

It is certified that error appears in the above-identified patent and that said Letters Patent is hereby corrected as shown below:

In column 13, line 27, in claim 1, after "within" insert -- a --.

In column 14, line 28, in claim 5, after "platform" (first instance) insert -- coordinate --.

Signed and Sealed this
Eighteenth Day of December, 2012

David J. Kappos
*Director of the United States Patent and Trademark Office*